(12) United States Patent
McChesney et al.

(10) Patent No.: US 7,935,067 B2
(45) Date of Patent: May 3, 2011

(54) ANCHORED ANKLE SUPPORT

(76) Inventors: John W. McChesney, Eagle, ID (US);
Louis E. Murdock, Boise, ID (US);
Mark DeBeliso, Marina, CA (US)

(*) Notice: Subject to any disclaimer, the term of this patent is extended or adjusted under 35 U.S.C. 154(b) by 46 days.

(21) Appl. No.: 12/134,654

(22) Filed: Jun. 6, 2008

(65) Prior Publication Data
US 2008/0306422 A1 Dec. 11, 2008

Related U.S. Application Data

(60) Provisional application No. 60/942,274, filed on Jun. 6, 2007.

(51) Int. Cl.
*A61F 5/00* (2006.01)
(52) U.S. Cl. .............................. 602/23; 602/26; 602/27
(58) Field of Classification Search .............. 602/23–29, 602/60–62; 128/882
See application file for complete search history.

(56) References Cited

U.S. PATENT DOCUMENTS

| | | | |
|---|---|---|---|
| 3,584,622 A | 6/1971 | Domenico | 128/166 |
| 4,345,590 A | 8/1982 | Nakajima | 128/166 |
| 4,729,370 A | 3/1988 | Kallassy | 128/166 |
| 4,753,229 A * | 6/1988 | Sutherland | 602/27 |
| 4,875,476 A | 10/1989 | Garcia | 128/157 |
| 5,050,620 A | 9/1991 | Cooper | 128/80 |
| 5,330,419 A * | 7/1994 | Toronto et al. | 602/27 |
| 5,431,623 A * | 7/1995 | Rice | 602/26 |
| 5,792,087 A | 8/1998 | Pringle | 602/27 |
| 5,833,640 A * | 11/1998 | Vazquez et al. | 602/27 |
| 6,117,098 A * | 9/2000 | Weber et al. | 602/27 |
| 6,126,625 A * | 10/2000 | Lundberg | 602/27 |
| 7,115,106 B2 | 10/2006 | Bodenschatz et al. | 602/65 |
| 7,267,656 B2 * | 9/2007 | Cooper | 602/27 |
| 2007/0060854 A1 | 3/2007 | Cropper | 602/27 |

* cited by examiner

*Primary Examiner* — Michael A. Brown
(74) *Attorney, Agent, or Firm* — Holland Law Office P.L.L.C.

(57) ABSTRACT

The present invention is directed to an anchored ankle brace including an anchor strap that connects an anchor member and ankle support member creating an increased resistance to lateral roll at the ankle. The ankle support member includes an ankle surround that surrounds and encloses at least a portion of the foot and an anchor member for positioning about the circumference above a midpoint of the lower leg characterized by a girth that is increasing as a distance from the ankle joint decreases. The anchored ankle brace also includes an anchor strap attached at a first end to the ankle support member and at a second end to the anchor member. The anchored ankle brace stabilizes the ankle joint increasing resistance to ankle sprain characterized by excessive inversion with planter flexion also known as "rolling the ankle".

16 Claims, 3 Drawing Sheets

ANCHORED ANKLE SUPPORT

RELATED APPLICATIONS

This application claims the priority of Provisional Application Ser. No. 60/942,274 entitled Anchored Ankle Support, filed Jun. 6, 2007, the content of said application being incorporated herein by reference.

FIELD OF THE INVENTION

This invention relates generally to devices and methods for stabilizing the ankle joint and surrounding ligament complex and more particularly to an ankle support that is stabilized by attachment about the proximal tibia, just distal to the knee.

BACKGROUND OF THE INVENTION

Traditionally, prophylactic ankle braces have utilized linear and diagonal strapping as well as various fastening systems, for instance laces or hook and loop closures, to provide static resistance to excessive sub-talar, ankle mortise, and mid-foot inversion and eversion. The most common athletic injury is the ankle sprain. Moreover, the most common mechanism injury (MOI) of ankle sprain is that of excessive inversion with planter flexion, also known as "rolling the ankle". Excessive inversion may damage the lateral collateral ligaments (LCL). Specifically, the LCL is comprised of the anterior talo-fibular, calcano-fibular and posterior talo-fibular ligaments of the ankle.

In attempt to protect this ligament complex, athletes, coaches, and medical professionals apply external, static structural support to the ankle by applying athletic adhesive tape or a brace. The purpose of this external support is to physically restrict ankle inversion. The previously mentioned linear and diagonal strapping found in the state of the art ankle braces affix or anchor these straps to the stocking-like body of the brace to establish support and resistance to excessive motion. Of these straps, the lateral strap plays the primary role in resisting inversion.

The typical lateral strap originates from the medial side of the hind or mid-foot and runs laterally under the foot and then up the lateral side of the lower leg, parallel to the distal one-third of the fibula. State of the art lateral straps terminate at the top of the brace. For that matter, all straps in all state of the art ankle braces terminate at the top of their respective braces. This is a point approximately two-thirds of the way down the shaft of the tibia, just below the muscle-tendon junction of the gastrocnemius.

Stability, characterized by resistance to inversion, arises from both the position of this lateral strap as well as from the fibers of the body of the brace that encompass the girth of the lower leg. The problem with deriving stability from these circumferential fibers at the top of the brace is that forces pulling distalward, for instance those forces observed during inversion, can cause downward slippage of the most proximal faces of the brace due to the decreasing girth of the lower leg at this point.

Accordingly, there is a need for an improved device and method for stabilizing the ankle joint and surrounding ligament complex. Therefore, one object of the present invention is to provide the aforementioned devices and methods for stabilizing the ankle joint and surrounding ligament complex.

SUMMARY OF THE INVENTION

The present invention relates to devices and methods for stabilizing the ankle joint and surrounding ligament complex and more particularly to an ankle support that is stabilized by attachment about the proximal end of the lower leg. Alternately, the present invention relates to a device and method for stabilizing the ankle joint and surrounding ligament complex and more particularly to an ankle support that is stabilized by attachment at a location below the knee joint line and above a midpoint or belly of the calf musculature.

An anchored ankle brace according to the present invention includes an ankle support member including an ankle-surround element that surrounds and encloses at least a portion of the foot and an anchor member adapted for positioning and attachment about a circumference of the proximal end of the lower leg, above a midpoint or belly of the calf musculature. This portion of the lower leg is characterized by a girth that is increasing as a distance from the ankle decreases. The anchored ankle brace of the present invention also includes an anchor strap attached at a first end to the ankle support member and at a second end to the anchor member.

The anchor member takes advantage of the enlarging girth of the calf to resist downward pulling force on the anchor member and the anchor strap, thereby improving performance of the anchored ankle brace, particularly over a period of time and as a result of strenuous activity typically encountered in physical activities. The net result is an observed improvement to resistance to excessive inversion and planter flexion and the associated damage to the lateral collateral ligaments.

In one embodiment, the anchor strap comprises a strap that extends along a lateral face of the lower leg between the ankle support member and the anchor member. An attachment element, for instance a ring or a buckle that allows selectively tensioning the strap, may be incorporated into the construction of the strap and the ankle support member or the anchor member. In one embodiment, a wearer inserts the end of the anchor strap through a ring fixed near the collar of the ankle support member pulling the strap to a desired tension. The end of the strap is secured by mating surfaces of hook and loop fabric. The wearer may adjust tension as desired or release the strap entirely as need dictates. Alternately, the anchor strap may be of a fixed length determined for a particular wearer.

In yet another embodiment of the anchored ankle brace, the anchor strap extends between the ankle support member and an anchor member configured as a knee brace. The knee brace serves the function of the anchor member inasmuch as at least some portion of every knee brace is positioned and attached about a circumference of the proximal end of the lower leg.

The foregoing has outlined rather broadly the features and technical advantages of the present invention so that the detailed description of the invention that follows may be better understood. Additional features and advantages of the invention will be described hereinafter, which form the subject of the invention. It should be appreciated by those skilled in the art that the conception and the specific embodiments disclosed might be readily used as a basis for modification or design of devices for carrying out the same purposes of the present invention. It should also be realized by those skilled in the art that such equivalent constructions do not depart from the spirit and scope of the invention as set forth herein.

BRIEF DESCRIPTION OF THE FIGURES

The accompanying figures which are incorporated in and form a part of the specification, illustrate embodiments of the present invention, and, together with the description, serve to explain the principles of the invention.

It is to be noted that the figures illustrate only typical embodiments of the invention and are therefore not to be considered limiting of its scope, for the invention will admit to other equally effective embodiments.

DETAILED DESCRIPTION OF THE INVENTION

Figure 1:
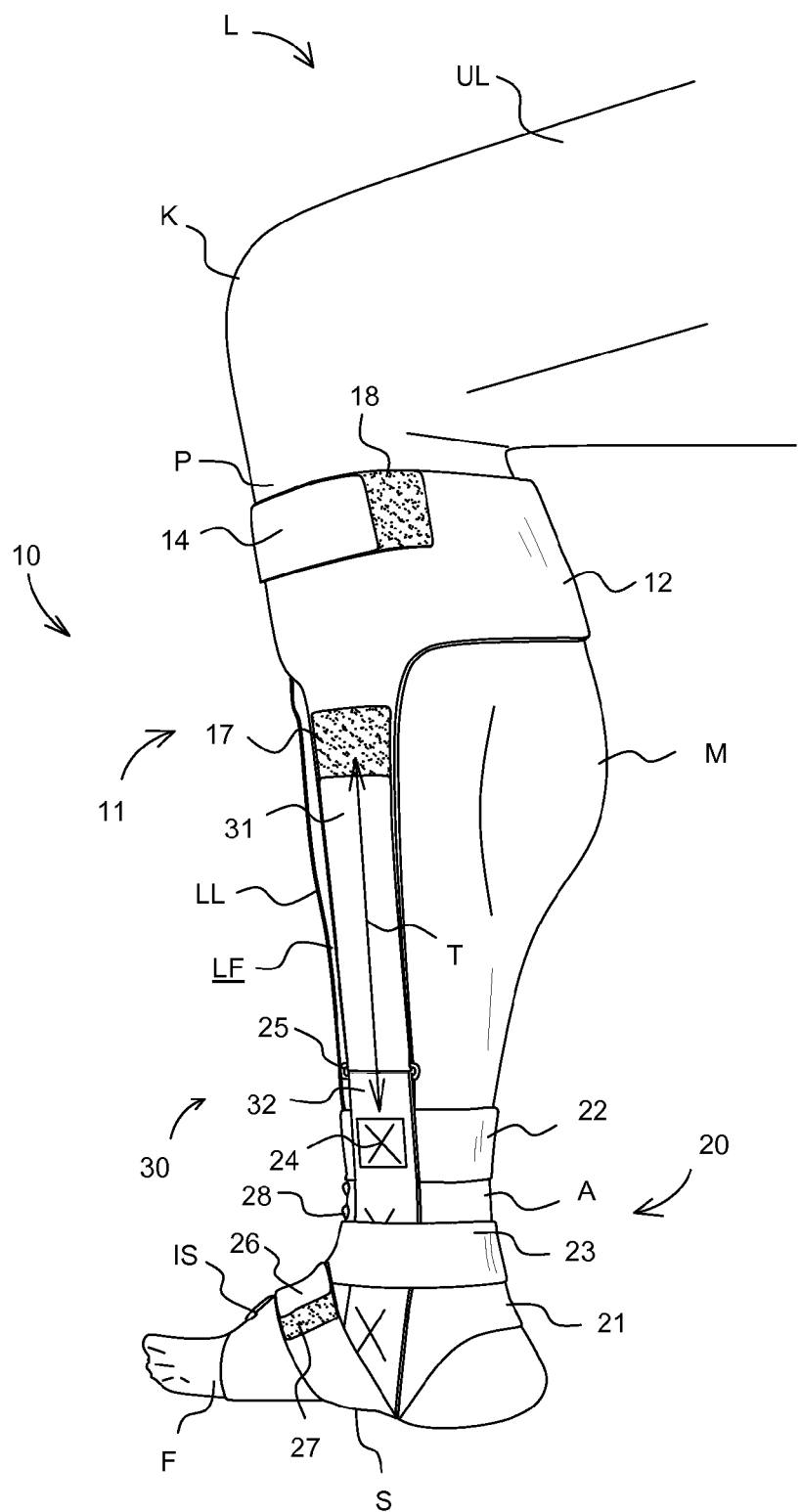
FIG. 1 is a representative perspective representation of an anchored ankle brace according to the present invention.

FIG. 1 is a representative side oblique view of a left leg L including upper leg UL and lower leg LL articulating at knee K. Leg L is defined in part by lateral face LF. Foot F, having sole S and instep IS, is attached to lower leg LL and articulates at ankle A. Anchored ankle brace 10 includes anchor strap 30 that connects anchor member 11 and ankle support member 20 creating an increased lateral roll resistance at ankle A. Ankle support member 20 includes lace-up ankle support 21 that surrounds and encloses a portion of ankle A and foot F. Lace-up ankle support 21 includes lacing closure 28. Lower anchor strap segment 32 is fixed to cuff 22 of lace-up ankle support 21 at stitching 24. Ring 25 is fixed at an upper end of lower anchor strap segment 32.

Anchored ankle brace 10 also includes anchor member 11. Anchor member 11 includes proximal leg band 12 positioned about proximal end P of lower leg LL, above a midpoint M of lower leg LL. Closure strap 14 allows adjustment and tightening of proximal leg band 12 about proximal end P of lower leg LL by attachment of the mating surfaces of hook fabric secured to the backside of closure strap 14, (not shown), with loop fabric 18 attached to proximal leg band 12.

Anchor strap 30 includes upper anchor strap segment 31 that extends down along lateral face LF of lower leg LL and is passed through ring 25 attached at an upper end of lower anchor strap segment 32. Tension T between upper anchor strap segment 31 and lower anchor strap segment 32, and therefore along anchor strap 30, is adjusted so that a desired tension T is established between ankle support member 20 and anchor member 11. Upper anchor strap segment 31 is secured by attachment of the mating surfaces of hook fabric, (not shown), with loop fabric 17 attached to upper anchor strap segment 31. When so fastened, anchor strap stabilizes ankle A by increasing lateral roll resistance at ankle A.

Figure 2:
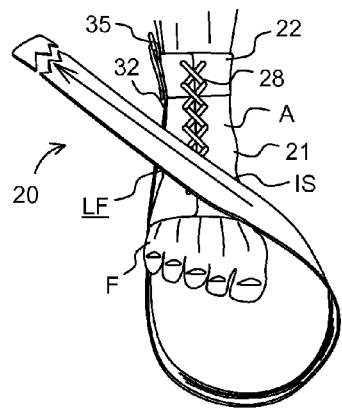
FIG. 2 is a representative front view of an ankle support member according to the present invention.

Referring to FIG. 2, lower anchor strap segment 32 of ankle support member 20 is shown as it is being wrapped about foot F, being drawn against the lateral face LF of foot F wrapping across the sole of foot F and over instep IS to be wrapped again around ankle A and foot F in any of a number of ways known to those skilled in the art.

Figure 3:
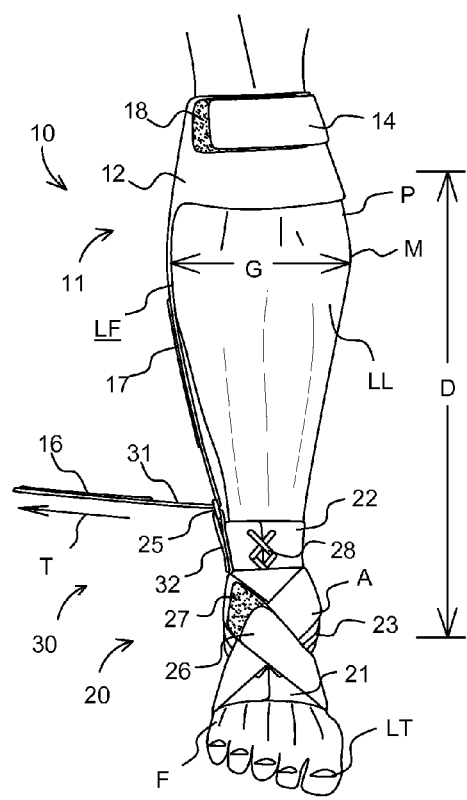
FIG. 3 is a representative front view of an anchored ankle brace according to the present invention.
Figure 4:
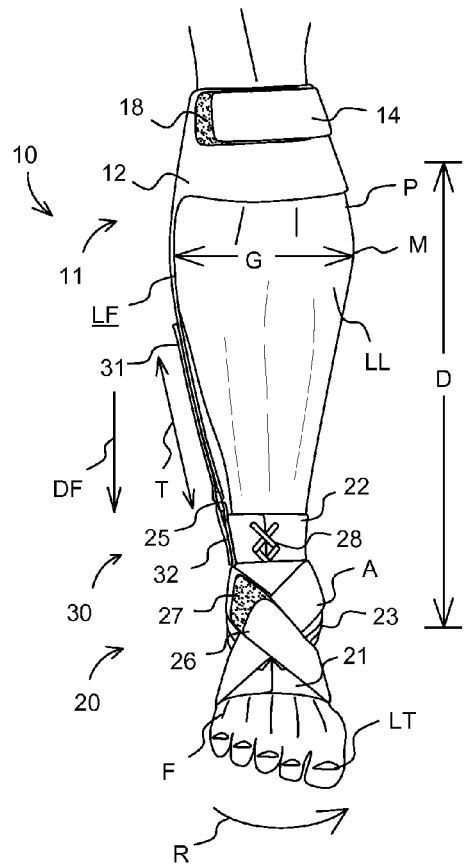
FIG. 4 is a representative front view of an anchored ankle brace according to the present invention.

Referring to FIGS. 3 and 4, representative front views of a lower leg LL including proximal end P and lateral face LF. Foot F, including large toe LT, is attached to and articulates with respect to lower leg LL, at ankle A. Anchored ankle brace 10 includes anchor strap 30 that connects anchor member 11 and ankle support member 20 creating an increased lateral roll resistance at ankle A. Ankle support member 20 includes lace-up ankle support 21 that surrounds and encloses a portion of ankle A and foot F. Lace-up ankle support 21 includes lacing closure 28. Lower anchor strap segment 32 is fixed to cuff 22 of lace-up ankle support 21. Ring 25 is fixed at an upper end of lower anchor strap segment 32.

Anchored ankle brace 10 also includes anchor member 11. Anchor member 11 includes proximal leg band 12 positioned about proximal end P of lower leg LL, above a midpoint M of lower leg LL characterized by a girth G that is increasing as a distance D from ankle A decreases. Closure strap 14 allows adjustment and tightening of proximal leg band 12 about proximal end P of lower leg LL by attachment of the mating surfaces of hook fabric, (not shown), secured to the backside of closure strap 14 with loop fabric 18 attached to proximal leg band 12.

Anchor strap 30 includes upper anchor strap segment 31 that is attached to and extends from proximal leg band 12 along lateral face LF of lower leg LL and is passed through ring 25 attached at an upper end of lower anchor strap segment 32. Lower anchor strap segment 32 extends along lateral face LF of ankle A and foot F, wrapping around ankle A and foot F forming wrap 23 which terminates at end 26. End 26 of lower anchor strap segment 32 attaches by means of mating hook fabric, (not shown), and loop fabric 27 attached to a surface of lower anchor strap segment 32. Tension T between upper anchor strap segment 31 and lower anchor strap segment 32, and therefore along anchor strap 30, is adjusted so that a desired tension T is established between ankle support member 20 and anchor member 11. Upper anchor strap segment 31 is secured by attachment of the mating surfaces of hook fabric, (not shown), with loop fabric 17 attached to upper anchor strap segment 31. Once upper anchor strap segment 31 is so secured to lower anchor strap segment 32 and tension T adjusted to a selected level, "rolling the ankle" indicated by the arrow R and an associated downward force DF against anchor strap 30 is resisted by anchor member 11.

Figure 5:
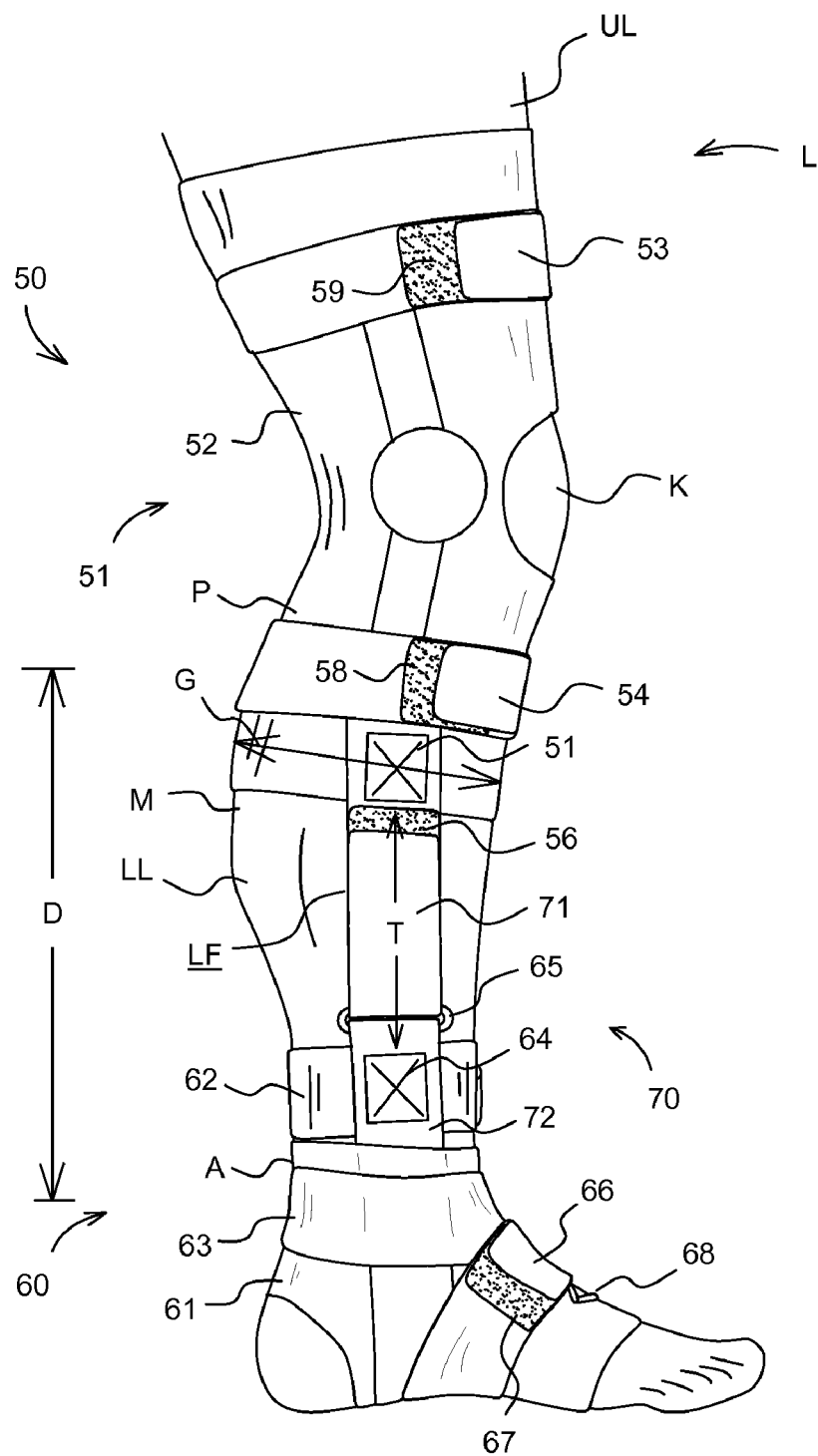
FIG. 5 is a representative side view of an anchored ankle brace according to the present invention.

FIG. 5 shows anchored ankle brace 50 worn on a right leg L, anchored ankle brace 50 including anchor member 51 attached to ankle support member 60 by anchor strap 70. Anchor member 51, in this alternate embodiment, is configured as a knee brace typical of any of a number of devices that are known, available and in wide use among athletes. Anchor member 51 includes sleeve 52 that is tubular in configuration and formed of an elastic fabric, fabricated to extend from a mid-thigh portion of upper leg UL to below knee K terminating above or proximate to midpoint M of the gastrocnemius located on lower leg LL. This portion of lower leg LL is characterized by a girth G that increases as a distance D from ankle A decreases.

Upper leg band 53 is positioned about upper leg UL and is secured after adjusting for tightness by attachment of the mating surfaces of hook fabric secured to the backside of upper leg band 53, (not shown), with loop fabric 59 attached to sleeve 52. Similarly, proximal leg band 54 is positioned about proximal end P of lower leg LL, above midpoint M of the gastrocnemius located on lower leg LL. Again, this portion of lower leg LL is characterized by a girth G that increases as a distance D from ankle A decreases. Proximal leg band 54 is secured after adjusting for tightness by attachment of the mating surfaces of hook fabric secured to the backside of proximal leg band 54, (not shown), with loop fabric 58 attached to sleeve 52.

Anchored ankle brace 50 also includes ankle support member 60 including lace-up ankle support 61 that surrounds and encloses a portion of ankle A and foot F. Lace-up ankle support 61 includes lacing closure 68. Lower anchor strap segment 72 is fixed to lace-up ankle support 61 by stitches 64. Ring 65 is fixed at an upper end of lower anchor strap segment 72. Lower anchor strap segment 72 extends along the lateral face LF of ankle A and foot F, wrapping around ankle A and foot F forming wrap 63 which terminates at end 66. End 66 of lower anchor strap segment 72 attaches by means of mating hook fabric, (not shown and loop fabric 67 attached to lower anchor strap segment 72.

Anchor strap 70 includes upper anchor strap segment 71 that is attached to and extends from proximal leg band 52 along lateral face LF of lower leg LL and is passed through ring 65 attached at an upper end of lower anchor strap segment 72. Lower anchor strap segment 72 extends along lateral face LF of ankle A and foot F, wrapping around ankle A and foot F forming wrap 63 which terminates at end 66. End 66 of lower anchor strap segment 72 attaches by means of mating hook fabric, (not shown), and loop fabric 67 attached to a surface of lower anchor strap segment 72. Tension T between upper anchor strap segment 71 and lower anchor strap segment 72, and therefore along anchor strap 70, is adjusted so that a desired tension T is established between ankle support member 60 and anchor member 51. Upper anchor strap segment 71 is secured by attachment of the mating surfaces of hook fabric, (not shown), with loop fabric 56 attached to upper anchor strap segment 71. Once upper anchor strap segment 71 is so secured to lower anchor strap segment 72 and tension T adjusted to a selected level, "rolling the ankle" indicated by the arrow R and an associated downward force DF against anchor strap 70 is resisted by anchor member 51.

While the invention has been described in connection with the preferred embodiment, it is not intended to limit the scope of the invention to the particular form set forth, but, on the contrary, it is intended to cover such alternatives, modifications and equivalents as may be included within the spirit and scope of the invention as defined by the appended claims.

What is claimed is:

1. An anchored ankle brace for stabilizing a lateral roll of a foot at an ankle joint with respect to a proximal end of a lower leg, the lower leg having a midpoint that is characterized by a belly of a gastrocnemius muscle connected to the lower leg, the lower leg, the ankle and the foot each defined partially by a lateral face, the anchored ankle brace comprising:
    an ankle support member that surrounds and encloses at least a portion of the foot;
    an anchor member including a proximal leg band adapted for placement about the proximal end of the lower leg proximal to the belly of the gastrocnemius muscle, the anchor member including a closure strap adapted for tightening the proximal leg band about the lower leg;
    an anchor strap having a length adapted to extend between the ankle support member and the anchor member along a lateral face of the lower leg, ankle and foot, the anchor strap including an upper anchor strap segment attached to the anchor member and a lower anchor strap segment attached to the ankle support member;
    the anchor member including an anchor strap attachment element, the second end of the anchor strap adapted to extend between the ankle support member and the anchor member along a lateral face of the lower leg, ankle and foot, the second end of the anchor strap attachable to the anchor strap attachment element; and
    means for adjusting a tension between the upper anchor strap segment and the lower anchor strap segment.

2. The anchored ankle brace of claim 1 wherein the ankle support member further comprises an ankle-surround element adapted to surround and enclose at least a portion of the foot and the ankle.

3. The anchored ankle brace of claim 1 wherein the ankle support member further comprises a lacing enclosure.

4. The anchored ankle brace of claim 1 wherein the ankle support member further comprises an enclosure including mating surfaces of hook and loop fabric.

5. The anchored ankle brace of claim 1 wherein the ankle support member further comprises an ankle wrap.

6. The anchored ankle brace of claim 1 wherein the anchor strap attachment element further comprises a D-ring.

7. The anchored ankle brace of claim 1 wherein the anchor member further comprises a knee brace.

8. The anchored ankle brace of claim 1 wherein the anchor member further comprises:
    a knee brace positioned above the midpoint of the lower leg;
    the knee brace including an upper leg band and a proximal leg band portion adapted for placement about the proximal end of the lower leg proximal to the belly of the gastrocnemius muscle, the proximal leg band portion including a closure strap adapted for tightening the proximal leg band portion about the proximal end of the lower leg.

9. An anchored ankle brace for stabilizing a lateral roll of a foot at an ankle joint with respect to a proximal end of a lower leg, the lower leg having a midpoint that is characterized by a belly of a gastrocnemius muscle connected to the lower leg, the lower leg, the ankle and the foot each defined partially by a lateral face, the anchored ankle brace comprising:
    an ankle support member that surrounds and encloses at least a portion of the foot;
    an anchor member including a proximal leg band adapted for placement about the proximal end of the lower leg proximal to the belly of the gastrocnemius muscle, the anchor member including a closure strap adapted for tightening the proximal leg band about the lower leg, the anchor member including a knee brace; and
    an anchor strap including an upper anchor strap segment attached to the anchor member and a lower anchor strap segment attached to the ankle support member, the lower anchor strap segment attachable to the upper anchor strap segment, the anchor strap having a length adapted to extend between the ankle support member and the anchor member along a lateral face of the lower leg, ankle and foot.

10. The anchored ankle brace of claim 9 wherein the anchor strap further comprises:
    an upper anchor strap segment attached to the anchor member;
    a lower anchor strap segment attached to the ankle support member; and
    means for attaching the upper anchor strap segment to the lower anchor strap segment and adjusting a tension between the upper anchor strap segment and the lower anchor strap.

11. The anchored ankle brace of claim 9 wherein the anchor strap further comprises:
    an upper anchor strap segment attached to the anchor member;
    a lower anchor strap segment attached to the ankle support member; and
    a ring attached to an upper end of lower anchor strap segment, the upper anchor strap segment passable through the ring, the upper anchor strap segment selectively tensionable.

12. The anchored ankle brace of claim 11 wherein the lower anchor strap further comprises a strap adapted to be drawn against the lateral face of the foot, wrapping beneath the foot and subsequently over the foot and around the ankle forming a wrap.

13. The anchored ankle brace of claim 9 wherein the ankle support member further comprises an ankle surround element adapted to surround and enclose at least a portion of the foot and the ankle.

14. The anchored ankle brace of claim 9 wherein the ankle support member further comprises an ankle wrap.

15. The anchored ankle brace of claim 9 wherein the anchor strap further comprises
   means for attaching the upper anchor strap segment to the lower anchor strap segment and adjusting a tension between the an upper anchor strap segment and the anchor strap segment.

16. The anchored ankle brace of claim 9 wherein the anchor strap further comprises a ring attached between an upper end of lower anchor strap segment and the upper anchor strap segment.

* * * * *